(12) United States Patent
Cheung et al.

(10) Patent No.: US 7,465,822 B2
(45) Date of Patent: *Dec. 16, 2008

(54) PROCESS FOR CARBONYLATION OF ALKYL ETHERS

(75) Inventors: Patricia Cheung, Berkeley, CA (US); Enrique Iglesia, Moraga, CA (US); John Glenn Sunley, East Yorkshire (GB); David John Law, East Yorkshire (GB); Aditya Bhan, Berkeley, CA (US)

(73) Assignees: BP Chemicals Ltd., Middlesex (GB); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/639,420

(22) Filed: Dec. 15, 2006

(65) Prior Publication Data

US 2007/0238897 A1 Oct. 11, 2007

Related U.S. Application Data

(63) Continuation-in-part of application No. 11/417,415, filed on May 3, 2006, now Pat. No. 7,309,798, which is a continuation-in-part of application No. 11/123,581, filed on May 5, 2005, now abandoned.

(51) Int. Cl.
*C07C 67/36* (2006.01)
*C07C 51/10* (2006.01)
(52) U.S. Cl. ..................... 560/232; 562/517
(58) Field of Classification Search ............... None
See application file for complete search history.

(56) References Cited

U.S. PATENT DOCUMENTS

| | | | |
|---|---|---|---|
| 3,689,533 A | 9/1972 | Schultz | |
| 4,612,387 A | 9/1986 | Feitler | |
| 5,189,203 A | 2/1993 | Hansen et al. | |
| 5,218,140 A | 6/1993 | Wegman | |
| 5,286,900 A | 2/1994 | Hansen et al. | |
| 5,420,345 A * | 5/1995 | Smith ................... | 562/519 |
| 5,728,871 A | 3/1998 | Joensen et al. | |
| 5,763,654 A | 6/1998 | Jones et al. | |
| 6,130,355 A | 10/2000 | Jones | |
| 6,353,132 B1 | 3/2002 | Zoeller et al. | |
| 6,355,837 B1 | 3/2002 | Zoeller et al. | |
| 6,387,842 B1 | 5/2002 | Wegman et al. | |
| 6,521,783 B1 | 2/2003 | Wegman et al. | |
| 2003/0054951 A1 | 3/2003 | Zoeller et al. | |

FOREIGN PATENT DOCUMENTS

| | | |
|---|---|---|
| DE | 3606 169 A1 | 8/1987 |
| EP | 0 566 370 A2 | 10/1993 |
| EP | 0 566 371 A2 | 10/1993 |
| EP | 0 596 632 A1 | 5/1994 |
| GB | 1185453 | 3/1970 |
| GB | 1277242 | 6/1972 |

OTHER PUBLICATIONS

Lamberti et al, Journal of the Chemical Society, Faraday Transactions, XANES, EXAFS and FTIR Characterization of Copper-Exchanged Mordenite, 1998, 94(10), pp. 1519-1525.*
Bagno, Alessandro et al; "Superacid-Catalyzed Carbonylation of Methane, Methyl Halides, Methyl Alcohol, and Dimethyl Ether to Methyl Acetate and Acetic Acid"; 1990, *J. Org. Chem.*, vol. 55, pp. 4284-4289.
Ellis, Brian et al; "Heterogeneous Catalysts for the Direct, Halide-free Carbonylation of Methanol"; 1996, *11th International Congress on Catalysis*; pp. 771-779.
Fujimoto, Kaoru et al; "Vapor Phase Carbonylation of Methanol with Solid Acid Catalysts"; 1984, *Chemistry Letters*; pp. 2047-2050.
Sardesai, Abhay et al; "Synthesis of Methyl Acetate from Dimethyl Ether Using Group VIII Metal Salts of Phosphotungstic Acid"; 2002, *Energy Sources*, vol. 24, pp. 301-317.
Volkova, G.G., et al; "Heterogeneous catalysts for halide-free carbonylation of dimethyl ether"; 2002, *Catalysts Letters*, vol. 80, No. 3-4, pp. 175-179.
Volkova, G.G., et al; "Solid superacids for halide-free carbonylation of dimethyl ether to methyl acetate"; 2004, *Elsevier B.V.*; 6 pages.
Wegman, Richard W., "Vapour Phase Carbonylation of Methanol or Dimethyl Ether with Metal-ion Exchanged Heteropoly Acid Catalysts"; 1994, *J. Chem. Soc., Chem. Commun.*; pp. 947-948.
Ferrierite—http://www.britannica.com/eb/article?tocId=9034104, 1 page.
Ferrierite-Mg. http://www.mindat.org/min-6931.html, 3 pages.
Ferrierite Mineral Data, http://webmineral.com/data/Ferriente.shtmt, 5 pages.
The Mineral Mordenite, http://mineral.galleries.com/galleries.com/minerals/silicate/mordenlt/mordenlt.htm, 2 pages.
Mordenite, http://www.minweb.co.uk/zeolites/morddata.html, 2 pages.
Co-pending U.S. Appl. No. 11/639,437, filed Dec. 15, 2006.
Baerlocher, C., et al; *The Atlas of Zoelite Framework Types*; 5th ed. Elsevier, <?xml:namespace prefix=st1 ns="urn:schemas-microsoft-com:office:smarttags" />Amsterdam, 2001—http://www.iza-structure.org/databases/.<?xml:namespace prefix=o ns="urn:schemas-microsoft-com:office:office" />.
Foster, M.D., et al; "A geometric solution to the largest-free-sphere problem in zeolite frameworks"; *Microphorous and Mesoporous Materials*; 90 (2006) pp. 32-38.

(Continued)

*Primary Examiner*—Paul A Zucker
(74) *Attorney, Agent, or Firm*—Nixon & Vanderhye, PC (57) ABSTRACT

A product comprising a lower alkyl ester of a lower aliphatic carboxylic acid is produced by a process comprising reacting under substantially anhydrous conditions a lower alkyl ether with carbon monoxide in the presence of a zeolite catalyst having an 8-member ring channel which is interconnected with a channel defined by a ring with greater than or equal to 8 members, the 8-member ring having a window size of at least 2.5 Angstroms×at least 3.6 Angstroms and at least one Brønsted acid site and the zeolite having a silica:$X_2O_3$ ratio of at least 5, wherein X is selected from aluminum, boron, iron, gallium and mixtures thereof.

41 Claims, 6 Drawing Sheets

OTHER PUBLICATIONS

Zones, S.I., et al; "Studies on the Role of Fluoride Ion vs Reaction Concentration in Zeolite Synthesis"; *J. Phys. Chem. B*. (2005) 109, pp. 652-661.

Vaughn, D.E.W., et al; "Synthesis of ECR-18—a synthetic analog of paulingite"; *Microporous Mesoporous Materials*; 28 (1999), pp. 233-239.

Barri, S.A.I., et al; "Structure of Theta-1, the first unidimensional medium-pore high-silica zeolite"; *Nature*, vol. 312, pp. 533-534 (1984).

Martucci, A., et al; "Crystal structure of zeolite omega, the synthetic counterpart of the natural zeolite mazzite"; *Microporous and Mesoporous Materials*; 63 (2003) pp. 33-42.

Bhat, S.D., et al; "High temperature hydrothermal crystallization, morphology and yield control of zeolite type K-LTL"; *Microphorous and Mesoporous Materials*; 76 (2004) pp. 81-89.

Ko, Y.S., et al; J. Ind. Eng. Chem., vol. 10, No. 4 (2004) pp. 636-644.

Howden, M.G.; "Synthesis of offertite: Part 1. Using various organic compounds as templates"; *Zeolites*; (1987), vol. 7, pp. 255-259.

Howden, M.G.; "Synthesis of offretite: Part 2. Using a combination of tetramethylammonium cations and monoethanolamine or 1,2-diaminoethane as template"; *Zeolites* (1987), vol. 7, pp. 260-264.

Makarova, M.A., et al; "Quantification of Bronsted Acidity in Mordenites"; *Journal of Catalysis*; vol. 172; pp. 170-177 (1997).

\* cited by examiner

Figure 1[a] – 1[b]. Methyl acetate formation rates on a) H-MOR (Silica/Alumina = 20), b) H-ZSM5 (Silica/Alumina = 24), c) H-Y (Silica/Alumina = 6), and d) H-FER (Silica/Alumina = 68) [930 kPa CO, 20 kPa DME, 50 kPa Ar].

Figure 1(c) – 1(d). Methyl acetate formation rates on a) H-MOR (Silica/Alumina = 20), b) H-ZSM5 (Silica/Alumina = 24), c) H-Y (Silica/Alumina = 6), and d) H-FER (Silica/Alumina = 68) [930 kPa CO, 20 kPa DME, 50 kPa Ar].

Figure 2. Acetic acid formation rates on H-MOR (Silica/Alumina = 20) [930 kPa CO, 20 kPa DME, 50 kPa Ar].

Figure 3. Methanol formation rates on H-MOR (Silica/Alumina = 20) [930 kPa CO, 20 kPa DME, 50 kPa Ar].

Figure 4. Hydrocarbon formation rates on H-MOR (Silica/Alumina = 20) [930 kPa CO, 20 kPa DME, 50 kPa Ar].

Figure 5. Product selectivities on H-MOR (Silica/Alumina = 20) [930 kPa CO, 20 kPa DME, 50 kPa Ar].

Figure 6. Methyl acetate rates on H-MOR (Silica/Alumina = 20) [465 kPa CO, 20 kPa DME, 25 kPa Ar, 500 kPa helium or 500 kPa hydrogen, 438 K].

Figure 7. Percentage of H+ sites in 8- and 12-member ring channels of H-mordenite calculated from peak deconvolution methods upon n-hexane dosing at 303K Figure 8. DME Carbonylation rates (438 K, 3.34 cm$^3$s$^{-1}$g$^{-1}$, 0.93 MPa CO, 20 kPa DME, 50 kPa Ar) plotted against the number of H$^+$ sites in 8-MR channels of MOR (▲) and FER (♦) and 12-MR channels of MOR (●). Inset shows DME carbonylation rates plotted against the total number of H$^+$ sites in these samples (✖).

PROCESS FOR CARBONYLATION OF ALKYL ETHERS

CROSS REFERENCE TO RELATED APPLICATIONS

This application is a continuation-in-part of U.S. patent application Ser. No. 11/417,415, filed May 3, 2006, now U.S. Pat. No. 7,309,798 which in turn is a continuation-in-part of U.S. patent application Ser. No. 11/123,581, filed May 5, 2005, now abandoned.

BACKGROUND OF THE INVENTION

This invention relates to an improved process for the production of methyl acetate from dimethyl ether, and more generally to the production of alkyl esters of aliphatic carboxylic acids, by the carbonylation of alkyl ethers. In another aspect this invention relates to the production of lower aliphatic carboxylic acids by first producing an alkyl ester from a lower alkyl ether, followed by hydrolysis of the ester to the acid. An example of this is the production of acetic acid by carbonylation of dimethyl ether, to form methyl acetate, followed by hydrolysis of the ester to produce acetic acid.

The most widely used industrial process for production of acetic acid is the carbonylation of methanol, which is described generally in British patents 1,185,453 and 1,277,242 and U.S. Pat. No. 3,689,533, for instance. In that type of process, methanol is reacted with carbon monoxide or a carbon monoxide-containing gas in the presence of a rhodium- or iridium-containing catalyst, in the additional presence of a halogen (usually iodine)-containing promoter. Though widely used, nonetheless these processes require the use of expensive corrosion-resistant alloys due to the presence of iodide and result in production of low levels of iodine-containing byproducts that are difficult to remove from the acetic acid by conventional distillation. Some non-halide based catalyst systems have been investigated for this reaction, but none have been commercialized, primarily due to issues with catalyst lifetime and selectivity.

Methyl acetate is an important compound used industrially in petrochemical processes, particularly as a feed for the production of acetic anhydride and/or acetic acid. Methyl acetate can also be used for the production of ethylidene diacetate, a precursor to vinyl acetate and polyvinyl acetate. Dimethyl ether may be readily produced from synthesis gas, and the cost of its production can be lower than that of methanol.

A number of patents describe processes in which methanol or a mixture of methanol and dimethyl ether is carbonylated in the presence of a catalyst. Typically the products are a mixture of acetic acid and methyl acetate, sometimes also including acetic anhydride. In those patents it is disclosed that one of the reactions that may occur is the carbonylation of dimethyl ether to form methyl acetate. Typically, however, dimethyl ether is not used as the sole or even as the primary component of the feed, but as a minor component in methanol streams.

For example, German OLS 3,606,169 of BASF AG discloses carbonylation of a mixture of methanol, methyl acetate and/or dimethyl ether to produce a product containing acetic acid, methyl acetate and/or dimethyl ether in the presence of a cobalt-containing zeolite catalyst. The preferred zeolites are those of the 10-ring pentasil type with pore sizes intermediate between those of 8-ring zeolite A and those of 12-ring zeolites X and Y.

Jones et al., U.S. Pat. No. 6,130,355, disclose a process for carbonylation of methanol and/or dimethyl ether to produce acetic acid using a catalyst composed of at least one Group VIII noble metal, a halogenated compound as cocatalyst, and an iodide salt as catalyst stabilizer. Other patents disclosing processes for production of acetic acid and/or methyl acetate, in which dimethyl ether may be present in the feed in a mixture with methanol include U.S. Pat. Nos. 6,353,132 and 6,355,837 and U.S. published application 2003/0054951, all of Zoeller et al. U.S. Pat. Nos. 5,189,203, 5,286,900 (both of Hansen et al.) and U.S. Pat. No. 5,728,871 (Joensen et al.) disclose processes in which syngas is first used to produce methanol, which is then combined with dimethyl ether, and the mixture carbonylated to produce acetic acid as a major product.

Several other references investigated carbonylation of dimethyl ether as the primary or sole component of a feed using various catalysts. For example, Jones et al. (U.S. Pat. No. 5,763,654) disclose such a process in which the catalyst is a Group VIII noble metal catalyst, with a halide-containing cocatalyst and methyl iodide as a promoter. Water was present in the reactor, though according to the disclosure of this patent it was used at lower concentrations than typical in the prior art. The major product was acetic acid.

Wegman (U.S. Pat. No. 5,218,140) experimented primarily with the carbonylation of methanol to produce acetic acid using heteropolyacid catalysts. The patent contains a group of experiments in which the feed was dimethyl ether (Examples 28-33); however, in those experiments the conversion to methyl acetate was relatively low.

Sardesai et al. (*Energy Sources* 2002, 24:301) also carried out carbonylation of dimethyl ether with a number of heteropoly acid catalysts, which gave results that varied widely in terms of conversion and selectivity to methyl acetate. Bagno et al. (*J. Org. Chem.* 1990, 55:4284) ran such a reaction with so-called "super-acid" catalysts including $BF_3$ and triflic acid, again with varying results as to selectively to methyl acetate.

BRIEF SUMMARY OF THE INVENTION

In brief, this invention comprises a process for producing a product comprising a lower alkyl ester of a lower aliphatic carboxylic acid comprising reacting a lower alkyl ether with carbon monoxide under substantially anhydrous conditions in the presence of a catalyst comprising a zeolite having at least one 8-member ring channel, said 8-member ring channel being interconnected with a channel defined by a ring with greater than or equal to 8 members, said 8-member ring having a window size of at least 2.5 Angstroms×at least 3.6 Angstroms and at least one Brønsted acid site and wherein the zeolite has a silica:$X_2O_3$ ratio of at least 5, wherein X is selected from aluminum, boron, iron, gallium and mixtures thereof, such as mordenite or ferrierite.

More specifically, the invention herein comprises a process for producing methyl acetate by reaction of dimethyl ether with carbon monoxide under substantially anhydrous conditions in the presence of a catalyst comprising a zeolite having at least one 8-member ring channel, said 8-member ring channel being interconnected with a channel defined by a ring with greater than or equal to 8 members, said 8-member ring having a window size of at least 2.5 Angstroms×at least 3.6 Angstroms and at least one Brønsted acid site and wherein the zeolite has a silica:$X_2O_3$ ratio of at least 5, wherein X is selected from aluminum, boron, iron, gallium and mixtures thereof, such as mordenite or ferrierite.

DETAILED DESCRIPTION OF THE INVENTION

In brief, this invention comprises a process for producing a product comprising a lower alkyl ester of a lower aliphatic carboxylic acid comprising reacting a lower alkyl ether with carbon monoxide under substantially anhydrous conditions in the presence of a catalyst comprising a zeolite having at least one 8-member ring channel, said 8-member ring channel being interconnected with a channel defined by a ring with greater than or equal to 8 members, said 8-member ring having a window size of at least 2.5 Angstroms×at least 3.6 Angstroms and at least one Brønsted acid site and wherein the zeolite has a silica:$X_2O_3$ ratio of at least 5, wherein X is selected from aluminum, boron, iron, gallium and mixtures thereof, such as mordenite or ferrierite.

More specifically, the invention herein comprises a process for producing methyl acetate by reaction of dimethyl ether with carbon monoxide under substantially anhydrous conditions in the presence of a catalyst comprising a zeolite having at least one 8-member ring channel, said 8-member ring channel being interconnected with a channel defined by a ring with greater than or equal to 8 members, said 8-member ring having a window size of at least 2.5 Angstroms×at least 3.6 Angstroms and at least one Brønsted acid site and wherein the zeolite has a silica:$X_2O_3$ ratio of at least 5, wherein X is selected from aluminum, boron, iron, gallium and mixtures thereof, such as mordenite or ferrierite.

One component of the feed to the process comprises (primarily) a lower alkyl ether, that is, a compound having the formula in which $R_1$ and $R_2$ are independently $C_1$-$C_6$ alkyl groups. The total number of carbon atoms in groups $R_1$ and $R_2$, if $R_1$ and $R_2$ are alkyl groups, is from 2 to 12, preferably from 2 to 8, most preferably from 2 to 6. Preferably, $R_1$ and $R_2$ are straight-chain alkyl groups, most preferably straight-chain alkyl groups having from 1 to 3 carbon atoms each.

The reaction overall can be depicted as

The term "alkyl" as used herein means a straight or branched chain, saturated aliphatic group, or a combination thereof, that has the number of carbon atoms designated (i.e. $C_3$ means three carbon atoms). Examples of acyclic alkyl groups include groups such as methyl, ethyl, n-propyl, isopropyl, n-butyl, t-butyl, isobutyl, sec-butyl, and the various pentyl and hexyl isomers.

The term "alkylene" as used herein refers to saturated aliphatic moieties that may form two single bonds with other moieties. This group includes, for example, methylene (—$CH_2$—), ethylene (—$CH_2CH_2$—) and hexylene [(—$CH_2$—)$_6$]. While alkylene groups may be straight or branched chain groups, straight-chain alkylene groups are preferred for use in the processes of this invention.

If the ether is a symmetrical ether, e.g. dimethyl ether, the main product will be the corresponding alkyl ester of an aliphatic acid (in this case, methyl acetate). If the ether is asymmetrical, the product will comprise one or both of the two possible carboxylic acid esters, depending on which of the two C—O bonds is cleaved in the reaction. For example, if the feed is methyl ethyl ether ($R_1$=methyl; $R_2$=ethyl), then the product will comprise ethyl acetate and/or methyl propionate.

A second component of the process is a feed comprising carbon monoxide. The feed may comprise substantially pure carbon monoxide (CO), for example, carbon monoxide typically provided by suppliers of industrial gases, or the feed may contain impurities that do not interfere with the conversion of the alkyl ether to the desired ester, such as hydrogen, nitrogen, helium, argon, methane and/or carbon dioxide. For example, the feed may comprise CO that is typically made commercially by removing hydrogen from synthesis gas via a cryogenic separation and/or use of a membrane.

The carbon monoxide feed may contain substantial amounts of hydrogen. For example, the feed may be what is commonly known as synthesis gas, i.e. any of a number of gaseous mixtures that are used for synthesizing a variety of organic or inorganic compounds, and particularly for ammonia synthesis. Synthesis gas typically results from reacting carbon-rich substances with steam (in a process known as steam reforming) or with steam and oxygen (a partial oxidation process). These gases contain mainly carbon monoxide and hydrogen, and may also contain smaller quantities of carbon dioxide and nitrogen. Suitably, the ratio of carbon monoxide:hydrogen may be in the range 1:3 to 15:1 on a molar basis, such as 1:1 to 10:1. The ability to use synthesis gas provides another advantage over processes for producing acetic acid from methanol, namely the option of using a less expensive carbon monoxide feed. In methanol-to-acetic acid processes, the inclusion of hydrogen in the feed can result in production of unwanted hydrogenation byproducts; accordingly the feed should be high-purity carbon monoxide.

The catalyst for use in the process of the invention is a zeolite. Zeolites, both natural and synthetic are microporous crystalline aluminosilicate materials having a definite crystalline structure as determined by X-ray diffraction. The chemical composition of zeolites can vary widely but they typically consist of $SiO_2$ in which some of the Si atoms may be replaced by tetravalent atoms such as Ti or Ge, by trivalent atoms such as Al, B, Ga, Fe or by bivalent atoms such as Be, or by a combination thereof. A zeolite is comprised of a system of channels which may be interconnected with other channel systems or cavities such as side-pockets or cages. The channel systems are uniform in size within a specific zeolite and may be three-dimensional but are not necessarily so and may be two-dimensional or one-dimensional. The channel systems of a zeolite are typically accessed via 12-member rings, 10-member rings or 8 member rings. The zeolites for use in the present invention contain at least one channel which is defined by an 8-member ring. Preferred zeolites are those which do not have side-pockets or cages within the zeolite structure. *The Atlas of Zeolite Framework Types* (C. Baerlocher, W. M. Meier, D. H. Olson, 5$^{th}$ ed. Elsevier, Amsterdam, 2001) in conjunction with the web-based version (http://www.iza-structure.org/databases/) is a compendium of topological and structural details about zeolite frameworks, including the types of ring structures present in the zeolite and the dimensions of the channels defined by each ring type. For the purposes of the present invention, the term 'zeolite' also includes materials having a zeolite-type structure such as delaminated porous crystalline oxide materials such as ITQ-6 and pillared layered oxide materials such as ITQ-36.

The process of the present invention employs a zeolite having at least one channel defined by an 8-member ring of tetrahedrally co-ordinated atoms (tetrahedra) with a window size having a minimum dimension of 2.5 Angstroms×3.6 Angstroms. The 8-member ring channel is interconnected with at least one channel defined by a ring with equal to or greater than 8 members, such as 10 and/or 12 members. The interconnected 8-, 10-, and 12-member ring channels provide access to Brønsted acid sites contained in the 8-member ring channels to enable the carbonylation of the lower alkyl ether, such as dimethyl ether to proceed at acceptable rates.

The zeolite for use in the present invention may consist of interconnected channels defined solely by 8-member rings, such as zeolites of framework type CHA, for example, chabazite and framework type ITE, for example ITQ-3. Preferably, however, the zeolite has at least one channel formed by an 8-member ring and at least one interconnecting channel defined by a ring with greater than 8 members, such as a 10, and/or 12 member ring. Non-limiting examples of zeolites having 8-member ring channels and interconnecting larger ring channel systems include zeolites of framework type MOR, for example, mordenite, FER, such as ferrierite and ITQ6, OFF, for example, offretite, GME, for example Gmelinite, MFS, such as ZSM-57, EON such as ECR-1 and ETR such as ECR-34. Preferably, the zeolites for use in the process of the present invention have at least one 8-member ring channel interconnected with at least one 12-member ring channel, such as those of framework type MOR, OFF and GME, for example, mordenite, offretite and gmelinite.

However, the mere presence of an interconnected 8-member ring channel in a zeolite is not sufficient to develop an effective carbonylation process. The window size of the channel systems also has to be controlled such that the reactant molecules can diffuse freely in and out of the zeolite framework. It has now been found that effective carbonylation can be achieved if the aperture (pore width) of an 8-member ring channel of the zeolite has a minimum dimension of 2.5×3.6 Angstroms. Channel dimensions of zeolite framework types may be found, for example, in the *Atlas of Zeolite Framework Types*. In addition, M. D. Foster, I. Rivin, M. M. J. Treacy and O. Delgado Friedrichs in "A geometric solution to the largest-free-sphere problem in zeolite frameworks" Microporous and Mesoporous Materials 90 (2006) 32-38, have used Delaunay triangulation methods applied to known zeolite frameworks and have tabulated the largest free-sphere diameters for diffusion along the three principal crystallographic directions for the 165 zeolite frameworks that are currently listed in the *Atlas of Zeolite Framework Types*. Ring window sizes may be modified by suitable atomic substitutions that change bond lengths and bond angles of the tetrahedrally co-ordinated atoms and the bridging oxygens.

A partial listing of zeolite framework types having at least one interconnected 8 member ring channel of minimum dimension of 2.5×3.6 Angstroms taken from *The Atlas of Zeolite Framework Types* is given below:

| MOR | Mordenite | 12 (6.5 × 7.0 Å) | 8 (3.4 × 4.8 Å) | 8 (2.6 × 5.7 Å) |
|-----|-----------|------------------|-----------------|-----------------|
| OFF | Offretite | 12 (6.7 × 6.8 Å) | 8 (3.6 × 4.9 Å) | |
| FER | Ferrierite | 10 (4.2 × 5.4 Å) | 8 (3.5 × 4.8 Å) | |
| CHA | Chabazite | 8 (3.8 × 3.8 Å) | | |
| ITE | ITQ3 | 8 (3.8 × 4.3 Å) | 8 (2.7 × 5.8 Å) | |
| GME | Gmelinite | 12 (7.0 × 7.0 Å) | 8 (3.6 × 3.9 Å) | |
| ETR | ECR-34 | 18 (10.1 Å) | 8 (2.5 × 6.0 Å) | |
| MFS | ZSM-57 | 10 (5.1 × 5.4 Å) | 8 (3.3 × 4.8 Å) | |
| EON | ECR-1 | 12 (6.7 × 6.8 Å) | 8 (3.4 × 4.9 Å) | 8 (2.9 × 2.9 Å) |

Zeolites are available from commercial sources. Alternatively they may be synthesized using known techniques. In general, synthetic zeolites are prepared from aqueous reaction mixtures comprising sources of appropriate oxides. Organic directing agents may also be included in the reaction mixture for the purpose of influencing the production of a zeolite having the desired structure. After the components of the reaction mixture are properly mixed with one another, the reaction mixture is subjected to appropriate crystallization conditions. After crystallization of the reaction mixture is complete, the crystalline product may be recovered from the remainder of the reaction mixture. Such recovery may involve filtering the crystals, washing with water followed by a calcination treatment at high temperature. The synthesis of zeolites is described in numerous references. For example, zeolite Y and its synthesis is described in U.S. Pat. No. 3,130,007, zeolite ZSM-23 is described in U.S. Pat. No. 4,076,842 and J. Phys. Chem. B, 109, 652-661 (2005), Zones, S. I. Darton, R. J., Morris, R and Hwany, S-J; ECR-18 is described in Microporous Mesoporous Mat., 28, 233-239 (1999), Vaughan D. E. W. & Strohmaier, K. G.; Theta-1 is described in Nature, 312, 533-534 (1984). Barri, S. A. I., Smith W. G., White, D and Young, D.; Mazzite is described in Microporous Mesoporous Mat., 63, 33-42 (2003), Martucci, A, Alberti, A, Guzmar-Castillo, M. D., Di Renzo, F and Fajula, F.; Zeolite L is described in Microporous Mesoporous Mat., 76, 81-99 (2004), Bhat, S. D., Niphadkair, P. S., Gaydharker, T. R., Awate, S. V., Belhekar, A. A. and Joshi, P. N and also in J. Ind. Eng. Chem. Vol. 10, No. 4 (2004), 636-644, Ko Y. S, Ahn W. S and offretite is described in Zeolites 255-264, Vol. 7, 1987 Howden M. G.

The zeolite catalyst for use in the process of the present invention is used in the acid form, generally referred to as the 'H' form of the zeolite, for example, H-mordenite, H-ferrierite. Other forms of the zeolite, such as the $NH_4$ form can be converted to the H-form, for example, by calcining the $NH_4$ form at elevated temperature. The acid form of a zeolite will possess Brønsted acid ($H^+$) sites which are distributed among the various channel systems in the zeolite. For example, H-mordenite has $H^+$ sites located in the 12 member ring channels and in the 8 member ring channels. The number or concentration of $H^+$ species residing in any particular channel system can be determined by known techniques such as infrared and NMR spectroscopic techniques. Quantification of Brønsted acidity by FTIR and NMR spectroscopy is described, for example, in Makarova, M. A., Wilson, A. E., van Liemt, B. J., Mesters, C. de Winter, A. W., Williams, C. Journal of Catalysis 1997, 172, (1), 170. The two types of channels in H-Mordenite (defined by 12 member rings and 8 member rings) give rise to at least two bands associated with the hydroxyl region of H-mordenite, one corresponding to vibration into the larger pores and the other, at a lower frequency, vibrating into the smaller pores. Work by the present inventors has shown that there is a correlation between the number of $H^+$ sites located in an 8-member ring channel and the carbonylation rate whereas no such correlation has been observed for 12-member ring channels. It has been found that carbonylation rates increase in parallel with the number of H$^+$ sites within 8 member ring channels. In contrast, no correlation is evident with the number of H$^+$ sites within 12 member ring channels. The number of H$^+$ sites within 8-member ring channels can be controlled by replacement of the H$^+$ with metal cations such as Na$^+$ or Co$^{2+}$ using known ion-exchange techniques.

The chemical composition of a zeolite may be expressed as involving the molar relationship:

$$SiO_2:X_2O_3$$

wherein X is a trivalent element, such as aluminum, boron, iron and/or gallium, preferably aluminum. The $SiO_2:X_2O_3$ ratio of a given zeolite is often variable. For example, it is known that mordenite can be synthesized with $SiO_2:Al_2O_3$ ratios of 6 to 90 or greater, zeolite Y, from about 1 to about 6, chabazite from about 2 to 2000 and gmelinite may be synthesised with $SiO_2:Al_2O_3$ ratios of greater than 4. In general, the upper limit of the $SiO_2:X_2O_3$ ratio is unbounded, for example, the zeolite ZSM-5. The zeolites for use in the present invention have a $SiO_2:X_2O_3$ molar ratio of at least 5, preferably in the range 7 to 40, such as 10 to 30. Suitably, the $SiO_2:X_2O_3$ molar ratio is less than or equal to 100. Particular $SiO_2:X_2O_3$ ratios can be obtained for many zeolites by dealumination (where X is Al), by standard techniques using high temperature steam treatment or acid washing.

In one embodiment the catalyst is composed of mordenite or ferrierite, or mixtures or combinations of the two, either per se (i.e., in the acid form, generally referred to as H-mordenite and H-ferrierite), or optionally ion-exchanged or loaded with one or more metals such as copper, nickel, iridium, rhodium, platinum, palladium, or cobalt. Mordenite catalysts may, in addition to silicon and aluminum atoms, contain further elements in the zeolite framework, particularly gallium and/or iron. Ferrierite catalysts may, in addition to silicon and aluminum atoms, contain further elements in the zeolite framework, particularly boron, gallium and/or iron. Framework modifier elements to both types of catalysts may be introduced to the framework by any conventional means. Where a framework modifier element is used in either a mordenite or ferrierite catalyst, the catalyst suitably has a ratio of silica to the oxide of the framework modifier element would be from about 10:1 to about 100:1. T-atom incorporation where T is B, Ga or Fe into zeolites of the ferrierite structure is disclosed in Melian-Cabrera et al., *Catalysis Today* 110 (2005) 255-263; Shawki et al., EP (Application) 234,766 (1987), Sulikowski et al., *J. Chem. Soc., Chem. Comm.*, 1289 (1989); Borade et al., *J. Chem. Soc., Chem. Comm.*, 2267 (1996); Jacob et al., *Zeolites* 430 (1993) Vol. 13. T-atom incorporation into zeolites of the mordenite structure where the T-atom is Ga or Fe is disclosed in Smith, WO 05/085162.

Mordenite (commonly available as Na-mordenite, NH$_4$-mordenite or H-mordenite) is a member of the aluminosilicate zeolite class of minerals. The formula of mordenite in its Na-form is usually given as Na(AlSi$_5$O$_{12}$).3H$_2$O or (Na$_2$,Ca, K$_2$)Al$_2$Si$_{10}$O$_{24}$.7H$_2$O. It is available from a number of commercial sources of such materials. H-Mordenite has elliptical 6.5×7.0 Å channels (12 member rings with window openings running in the crystallographical c-direction). It also has a system of smaller channels running perpendicular to the 12 member ring channels (and running in the b-direction). These small channels consist of 3.4×4.8 Å channels having 8 member ring windows of these dimensions. The mordenite structure also possesses a zig-zag Y-branching of the pore structure due to twisted 8 member rings (in the crystallographic c-direction) This results in a distorted window to each side of the Y-branching of 2.6×5.7 Å. Ferrierite is another member of the aluminosilicate zeolite class of minerals, also available in the Na—, NH$_4$— and H— forms. In the Na-form its formula generally is given as Na$_{0.8}$K$_{0.2}$MgSi$_{15}$Al$_3$O$_{36}$.9H$_2$O or (Mg, Na$_2$,K$_2$,Ca)$_{3-5}$Mg[Al$_{5-7}$Si$_{27.5-31}$O$_{72}$].18H$_2$O. It, too, is available from various commercial sources. Additional information on these and other materials can be found on the website of the International Zeolite Association, www.iza-online.org. H-Ferrierite has 4.2×5.4 10-member ring channels running in the crystallographic c-direction and 3.5×4.8 8-member ring channels running in the b-direction.

Because the reaction is to be conducted substantially in the absence of water, the catalyst should be dried before beginning the operation, for example, by preheating to 400-500° C.

In general, the process is run at temperatures at or below about 250° C., that is, at temperatures of from about 100 to about 250° C., preferably from about 150 to about 180° C. One feature of the process is that, surprisingly, the carbonylation of dimethyl ether (DME) to methyl acetate using mordenite zeolite based catalysts and in the substantial absence of water can be performed with very high selectivities at temperatures significantly lower than those cited in the prior art for methanol carbonylation. Additionally, under these conditions the mordenite is essentially inactive for the carbonylation of methanol. Reaction temperatures are kept within the above range also to minimize the dehydration of any methanol that may be present to form hydrocarbons and water, because the presence of water strongly inhibits the carbonylation of dimethyl ether to methyl acetate.

Typical total operating pressures are from about 1 bar to about 100 bar, preferably with carbon monoxide pressures greater than 10 bar and dimethyl ether pressures below 5 bar.

The process is carried out under substantially anhydrous conditions, i.e. in the substantial absence of water. The carbonylation of dimethyl ether to methyl acetate does not generate water in-situ. Water has been found to inhibit the carbonylation of dimethyl ether to form methyl acetate. This is in comparison to prior art processes in which dimethyl ether was a co-feed, and in which water was also fed to the reaction. Water is thus kept as low as feasible, in order to allow the desired reaction to proceed best. To accomplish this, the ether and carbon monoxide reactants and the catalyst are preferably dried prior to introduction into the process.

The process may be run as either a continuous or a batch process, with continuous processes typically preferred. Essentially, the process is a gas-phase operation, with reactants being introduced in either liquid or gaseous phase and products withdrawn as gases. As desired, the reaction products may subsequently be cooled and condensed. The catalyst may be used as convenient, in either a fixed bed or a fluidized bed. In operating the process, unreacted starting materials may be recovered and recycled to the reactor. The product methyl acetate it may be recovered and sold as such, or may be forwarded to other chemical process units as desired. If desired, the entire reaction product may be sent to a chemical process unit for conversion of the methyl acetate and optionally other components to other useful products.

In one preferred embodiment of the invention, the methyl acetate is recovered from the reaction products and contacted with water to form acetic acid via hydrolysis reactions. Alternatively, the entire product may be passed to a hydrolysis step, and acetic acid separated thereafter. The hydrolysis step may be carried out in the presence of an acid catalyst, and may take the form of a reactive distillation process, well known in the art.

After separation, alcohols produced in the hydrolysis reactor may be sent to a dehydration reactor to produce an ether, which can be separated from water and recycled to the carbonylation unit as fresh feed for the carbonylation reactor.

In another embodiment, the hydrolysis of the ester product to alcohol and carboxylic acid is performed by injecting water at one or more points in the catalyst bed, once a significant amount of ester has been produced by carbonylation. Injection of water in this manner essentially stops the conversion of dimethyl ether to methyl acetate, and removes the requirement for a separate hydrolysis reactor. The mordenite or ferrierite catalyst thus may also function as the acid catalyst for the hydrolysis of the ester product to give a carboxylic acid. If the reactor is a fluidized bed reactor, operating in the transport regime, with back-mixing, then the reactor and catalyst will then have to be thoroughly dried before they are again used for the main process. If, on the other hand, the reactor is a tubular reactor, with staged introduction of water downstream of the main reaction zone, such drying should not be necessary.

Using a mordenite catalyst, conversions can be up to 100%, preferably from about 10% to about 100%, depending on the space velocity and reactant pressures used. Selectivity to methyl acetate has been shown to be constant, at values greater than 99% at 165° C. for more than 10 hours. At 190° C., selectivities to methyl acetate are initially 96%, but decrease with time on stream. Such results are unexpected with the use of mordenite, and maintenance of a substantially anhydrous environment, as the prior art indicates that mordenite typically must be used for the conversion of methanol to acetic acid at temperatures substantially higher than 250° C. Such temperatures also can lead to deactivation of methanol carbonylation due to the formation of hydrocarbons, which can block catalyst pores and/or active sites. In addition, as will be seen in the Examples, experiments with other zeolites under similar conditions do not show the desired conversion and/or selectivity as mordenite and ferrierite.

Furthermore, as compared to prior art processes, there is relatively little product gasoline and/or other higher hydrocarbons. Often when methanol is used as a feed, there is a so-called "MTG" (methanol-to-gasoline) reaction that produces an undesirable high level of such hydrocarbons. Formation of methanol can occur in the early stages of the reaction; however, this can be minimized by pretreating the catalyst bed with dimethyl ether at typical reaction temperatures.

The following examples are presented as illustrative of the invention. However, they are not meant to limit the scope of this invention.

General Procedures A

1) Catalyst Preparation A

Catalysts were obtained commercially in the ammonium or acid form and pretreated in flowing dry air at 773 K for 3 hours.

| Catalyst | Source | Silica/Alumina Ratio (SAR) | Channel Structure |
|---|---|---|---|
| H-MOR (mordenite) | Zeolyst International | 20 | 12 (6.5 × 7.0 Å) 8 (3.4 × 4.8 Å) 8 (2.6 × 5.7 Å) |

-continued

| Catalyst | Source | Silica/Alumina Ratio (SAR) | Channel Structure |
|---|---|---|---|
| H-MOR (mordenite) | Zeolyst International | 90 | 12 (6.5 × 7.0 Å) 8 (3.4 × 4.8 Å) 8 (2.6 × 5.7 Å) |
| H-FER (ferrierite) | Zeolyst International | 68 | 10 (4.2 × 5.4 Å) 8 (3.5 × 4.8 Å) |
| H-ZSM5 | Al—Si Penta Zeolithe GmbH | 25 | 10 (5.1 × 5.5 Å) 10 (5.3 × 5.6 Å) |
| H—Y | Engelhard Corporation | 6 | 12 (7.4 × 7.4 Å) |
| amorphous $SiO_2$—$Al_2O_3$ | Sigma-Aldrich | 12 | None |

2) Dimethyl Ether Carbonylation Reaction A

Dimethyl ether carbonylation reactions were carried out in a fixed-bed stainless steel microreactor using 0.15-0.5 g catalyst. Catalysts were activated at 773 K in flowing dry air for 2 hours, cooled to reaction temperatures (150-240° C.), flushed with flowing dry helium, and pressurized to 10 bar before introducing reactants. The reactant mixture consisted of 20 kPa dimethyl ether, 930 kPa carbon monoxide, and 50 kPa argon, the latter as an internal standard (1 bar=101 kPa). All pretreatment and reactant streams were dried by passing through a calcium hydride bed (0.5 g, Aldrich) placed immediately before the reactor. Heat-traced lines (200-250° C.) were used to transfer the reactants and products to an on-line mass spectrometer (MKS Spectra Minilab) and to a gas chromatograph (Agilent 6890) equipped with flame ionization and thermal conductivity detectors with methyl siloxane and Porapak® Q columns, respectively.

3) Dimethyl Ether Carbonylation Reaction with Synthesis Gas

Hydrogen addition experiments were carried out in the flow reactor described above. The reactant mixture consisted of 10 kPa dimethyl ether, 465 kPa carbon monoxide, 25 kPa argon, and 500 kPa helium or hydrogen. Helium, an unreactive diluent, was replaced by hydrogen after the catalyst system reached steady-state.

Experiments were conducted using the above-described procedure for carbonylation of dimethyl ether over seven catalysts in the temperature range of 148-335° C., with most experiments being conducted at 150-240° C., and 9.3 bar carbon monoxide. Catalysts included mordenite (H-MOR; Silica/alumina ratio (SAR)=20 and SAR=90), zeolite MFI (H-ZSM5; SAR=25), Y faujasite (H—Y; SAR=6) ferrierite (H-FER; SAR=68), and amorphous silica-alumina (SAR=12). Experimental conditions were: 10 bar total pressure, total flow=100 cm³ (STP)/min, 2% DME/5% Ar/93% CO feed (passed over 0.5 g $CaH_2$ pre-reactor drying bed at ambient temperature) while increasing the temperature in steps between 144 and 335° C.

Figure 1:
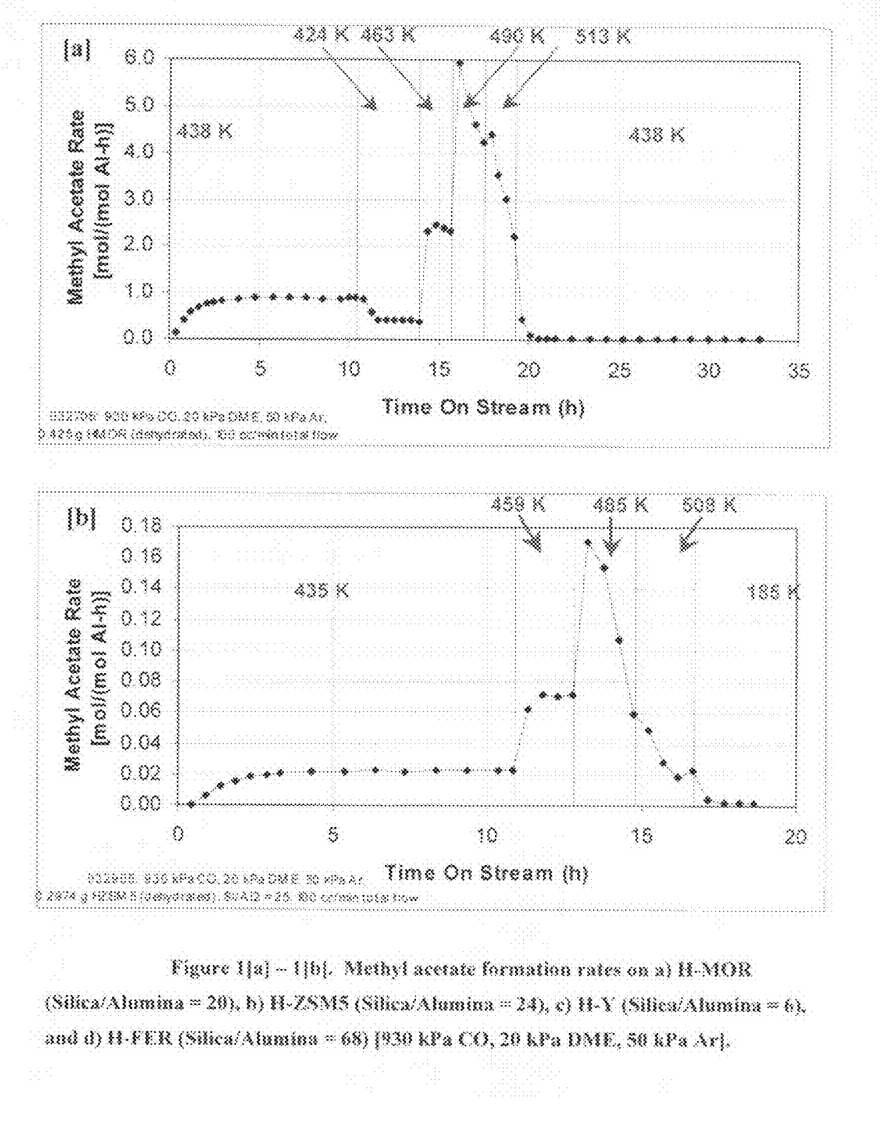
FIG. 1 depicts formation rates of methyl acetate using various zeolites as catalyst candidates for the process of this invention.
Figure 1C:
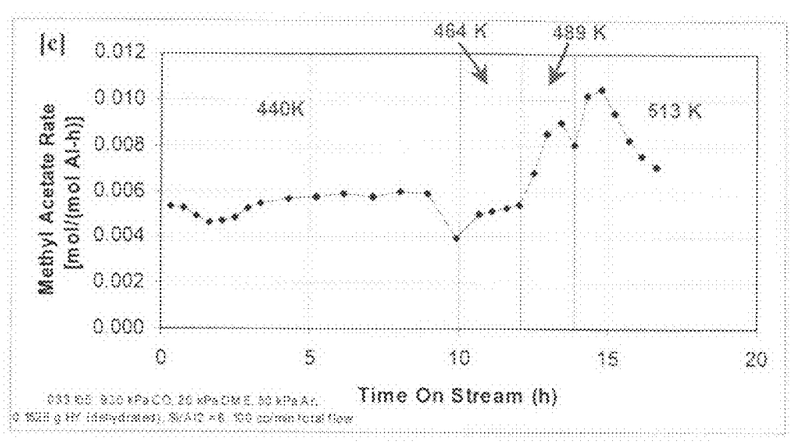
Figure 1D:
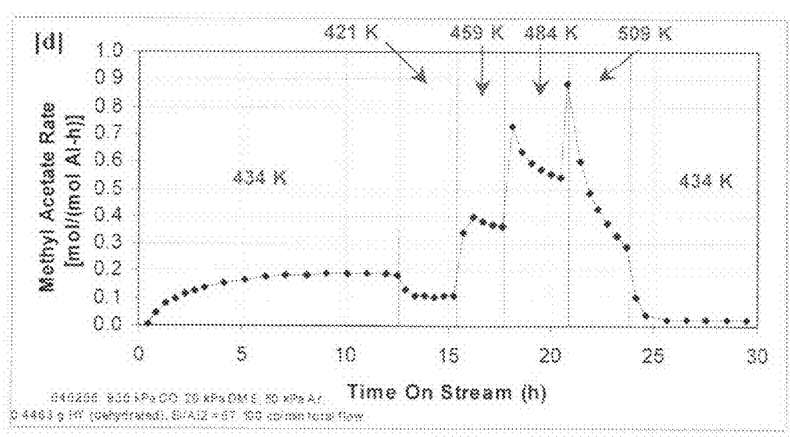

These experiments demonstrate that mordenite and ferrierite are far superior to other zeolite candidates not containing 8-member ring channels for dimethyl ether carbonylation. Methyl acetate formation rates are shown in FIG. 1. Under the reaction conditions, rates at ~165° C. (normalized per total Al) on H-MOR were nearly 50 times greater than those on H-ZSM5 and more than 150 times greater than those on H—Y. No deactivation was observed on any of the three zeolites at temperatures between 150 and 190° C. At higher temperatures (≧488 K(≧215° C.)), methyl acetate rates decreased with time on-stream, apparently as a result of the significant formation of large unreactive organic residues.

This, if sufficiently extensive, can prevent the catalysts from returning to their initial carbonylation rates when tested again at lower temperatures (165-185° C.).

On H—Y at temperatures ≧488 K, the reactor effluent contained a broad range of hydrocarbons including several that overlapped with methyl acetate and methanol in the gas chromatogram. Therefore, at these temperatures, the reported methyl acetate and methanol formation rates on H—Y may be somewhat larger than their true formation rates.

Figure 2:
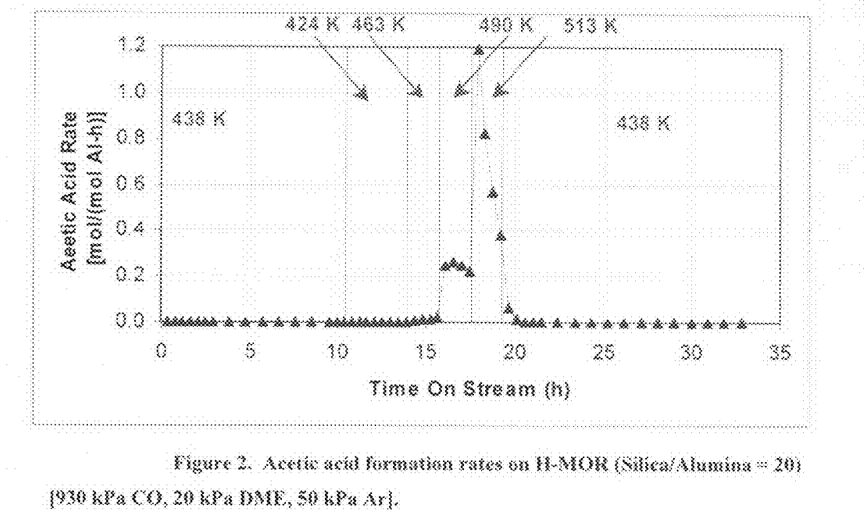
FIG. 2 depicts the formation rate of acetic acid using an H-mordenite zeolite catalyst for the process of this invention.
Figure 3:
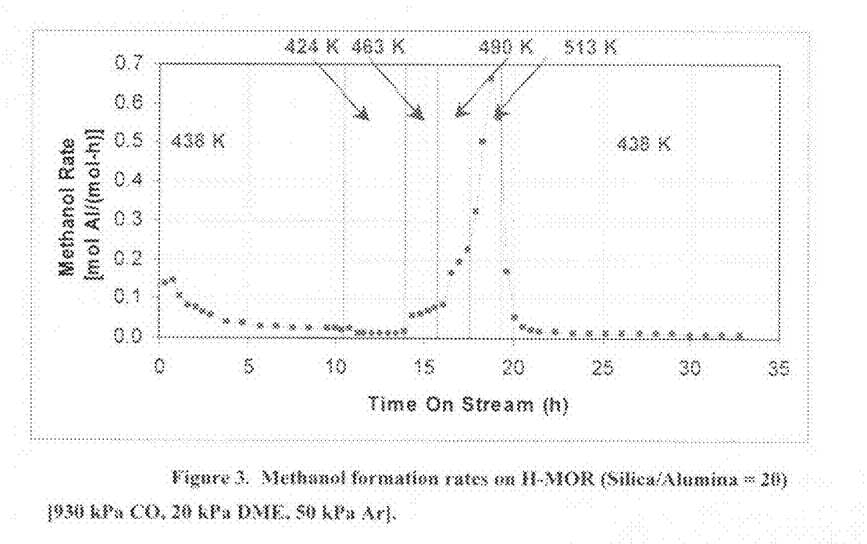
FIG. 3 depicts the formation rate of methanol using an H-mordenite zeolite catalyst for the process of this invention.
Figure 4:
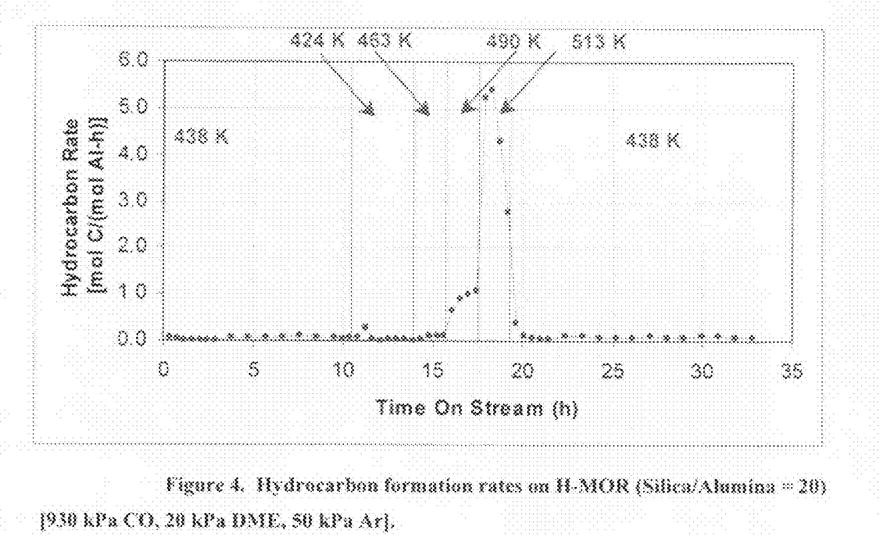
FIG. 4 depicts the formation rate of hydrocarbons using an H-mordenite zeolite catalyst for the process of this invention.
Figure 5:
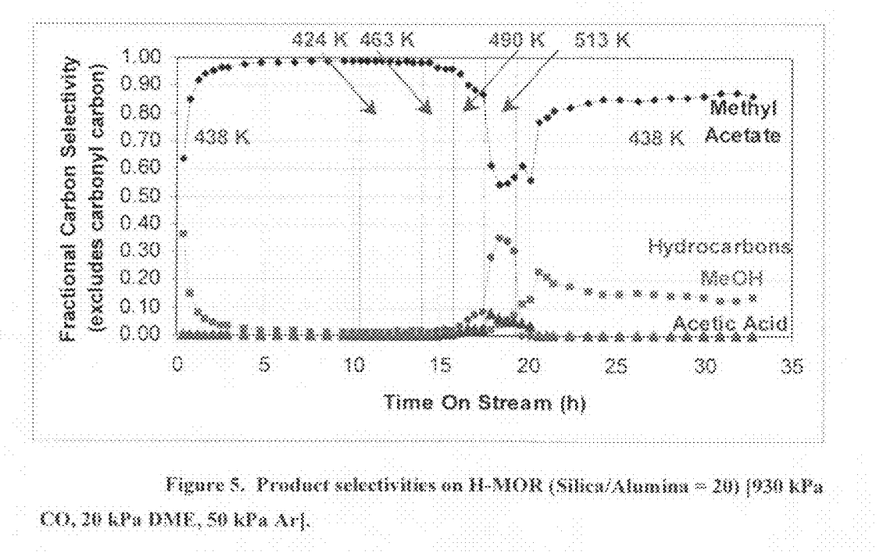
FIG. 5 depicts calculated product selectivities.

FIGS. 2 and 3 show acetic acid and methanol formation rates on H-MOR. Acetic acid forms via methyl acetate hydrolysis or methanol carbonylation at temperatures ≧490 K on H-MOR. Methanol cannot form from dimethyl ether in the absence of water, which may be formed, however, as a by-product of MTG (methane-to-gasoline) reactions. The initial methanol formation rates reflect reactions of either residual water or of water formed from hydroxyl groups remaining in zeolites after catalyst pre-treatment (drying) at 500° C. Therefore, when detectable steady-state methanol rates are observed above 463 K, hydrocarbons are presumably being formed, even if they are not detected in the effluent by gas chromatography. Hydrocarbon formation rates (calculated as the dimethyl ether converted to products other than methyl acetate, acetic acid, or methanol) on H-MOR are shown in FIG. 4. No acetic acid was observed on the other zeolites. Product selectivities are shown in FIG. 5.

Low-aluminum content H-MOR(SAR=90) and amorphous silica alumina (SAR=12) were also tested over a broad range of temperatures (160-335° C.).

Carbonylation rates (per Al) on low aluminum content H-MOR were an order of magnitude smaller than those reported for the higher aluminum content H-MOR(SAR=20). The lower carbonylation activity (per Al) is not completely unexpected for this material because it shows higher hydrocarbon formation rates. Methanol (and DME)-to-hydrocarbon reactions form water in stoichiometric amounts; our studies have shown the requirement of anhydrous conditions for carbonylation activity. A dry environment is not possible in the presence of concurrent reactions that form hydrocarbons.

Amorphous silica-alumina (surface area=440 m$^2$/g) was also tested, for comparison with zeolitic materials. It began to show slight carbonylation activity at 259° C. Carbonylation rates on this material are 3-4 orders of magnitude lower than on H-MOR(SAR=20) at this temperature. A summary of the above-described tests is presented below in Table 1.

TABLE 1

Steady-state product formation rates and acetyl carbon selectivity.

|  | T(K) | Acetyl Rate [mol/(mol Al-h)] | MeOH Rate [mol/(mol Al-h)] | Hydrocarbon Rate [mol C/(mol Al-h)] | Acetyl Carbon Selectivity (%)** |
|---|---|---|---|---|---|
| H-MOR Si/Al = 10 0.425 g | 424 | 0.4 | 0.011 | 0 | 99 |
|  | 438 | 0.9 | 0.023 | 0 | 99 |
|  | 463 | 2.7 | 0.055 | 0.02 | 96 |
|  | 490 | 7.1* |  |  |  |
|  | 513 | deactivates |  |  |  |
| H-FER Si/Al = 34 0.446 g | 421 | 0.11 | 0 | 0 | 100 |
|  | 434 | 0.19 | 0.012 | 0 | 97 |
|  | 459 | 0.40 | 0.045 | 0 | 94 |
|  | 484 | 0.73* |  |  |  |
|  | 509 | deactivates |  |  |  |
| H-ZSM5 Si/Al = 6 0.297 g | 435 | 0.023 | 0.116 | 0.22 | 12 |
|  | 459 | 0.072 | 0.338 | 0.52 | 14 |
|  | 485 | 0.171* |  |  |  |
|  | 508 | deactivates |  |  |  |
| H—Y Si/Al = 3 0.153 g | 440 | <0.01 | 0.14 | 0.22 | 3 |
|  | 464 | <0.01 | 0.38 | 0.86 | <1 |
|  | 489 | <0.01 |  |  |  |
|  | 513 | ~0.01 |  |  |  |
| H-MOR Si/Al = 45 .427 g | 433 | 0.065 | 0.096 | 0.22 | 29 |
|  | 451 | 0.125 | 0.27 | 0.3 | 30 |
|  | 471 | 0.233 | 0.68 | 0.96 | 22 |
|  | 492 | 0.425 | 1.52 | 3.9 | 14 |
|  | 506 | 0.696 | 2.49 | 5.3 | 15 |
| Amorphous Silica Alumina Si/Al = 6 .5476 g | 438 | 0 | 0 | 0 | 0 |
|  | 485 | 0 | 0 | 0 | 0 |
|  | 532 | 0.004 | 0.012 | 0.05 | 11 |
|  | 582 | 0.05 | 0.23 | 0.15 | 21 |
|  | 608 | 0.1 | 0.4 | 0.18 | 26 |

Figure 6:
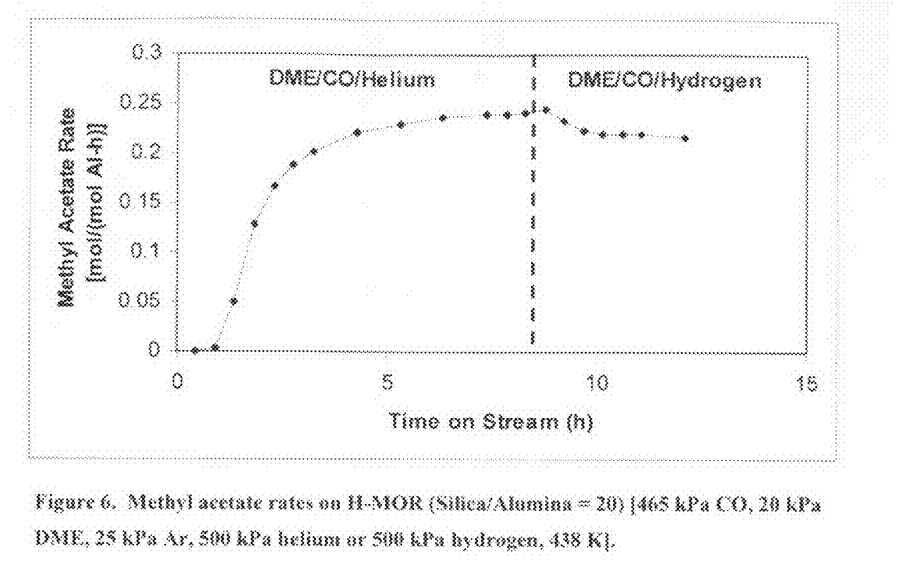
FIG. 6 depicts the formation rate of methyl acetate using H-mordenite zeolite catalyst in the presence (and absence) of hydrogen in the reactant mixture.

*Acetyl formation rates after 25 minutes at corresponding temperature, catalyst deactivates.
**Acetyl carbon selectivity does not include carbonyl carbon Studies with Synthesis Gas H-Mordenite was evaluated for dimethyl ether carbonylation in the presence of hydrogen. Carbonylation rates are essentially unaffected by the presence of hydrogen as one-half of the total reactant feedstock (FIG. 6). Synthesis gas of various hydrogen:carbon monoxide ratios can be utilized without affecting dimethyl ether carbonylation rates.

Incorporated of Framework Metals (GaAl/Si)NH$_4$-mordenite (SiO$_2$:Ga$_2$O$_3$~39.2 and SiO$_2$:Al$_2$O$_3$~19.4) was converted from the ammonium form and tested for DME carbonylation under the following conditions. The sample was treated in flowing dry air (3.33 cm$^3$s$^{-1}$) at 773 K (0.0167 K s$^{-1}$) for 3 hours to convert it from the NH$_4^+$ form to the H$^+$ form. DME carbonylation rates were measured in a packet-bed stainless steel reactor (8.1 mm ID, 9.5 mm OD) held within a three-zone resistively heated furnace. The catalyst sample (0.5 g, 185-250 mm particle diameter) was treated in flowing dry air (~1.67 cm$^3$s$^{-1}$ g$^{-1}$, zero grade, Praxair) for 3 h at 773 K (0.0167 K s$^{-1}$) before cooling in flowing He (~3.33 cm$^3$s$^{-1}$g$^{-1}$, UHP Praxair) to reaction temperature (438 K) and a mixture of 2% DME/5% Ar/93% CO (99.5% DME, Praxair; UHP Ar/CO, Praxair) was then introduced into the reactor at ~1.67 cm$^3$ s$^{-1}$.

The catalytic results were compared to H-mordenite (H-MOR) tested under the same conditions, in Table 2.

TABLE 2

Comparison of (GaAl/Si)H-mordenite and (Al/Si)H-mordenite samples

| | (GaAl/Si)H-mordenite | H-mordenite (Zeolyst International; SAR = 20) |
|---|---|---|
| Rate [mol((g-atom Al)h)$^{-1}$] | 0.54 | 0.9 |
| Space Time Yield [g-MeOAc((g-zeolite)h)$^{-1}$] | 0.061 | 0.103 |

α 930 kPa CO, 20 kPa DME, 50 kPa Ar, 438 K

Silica/Alumina Molar Ratio (SAR)

A series of runs was carried out using catalysts with various silica:alumina molar ratios. Table 3 contains a list of H-MOR samples and corresponding rates [mol((g-atom Al)h)$^{-1}$] and space time yields [g-MeOAc((g-zeolite)h)$^{-1}$]. Typically 0.5 g of sample was used at 438 K with total pressures of 10 Atm (20 kPa DME, 50 kPa Ar, 930 kPa CO) and a flow of 1.67 cm$^3$ s$^{-1}$. These showed some quite good rates in terms of mol kg$^{-1}$ h$^{-1}$. The results show that the productivity per mass of catalyst (and presumably volume) can be increased by changing the silica to alumina ratio.

TABLE 3

DME Carbonylation Rates and Space Time Yields as a function of Al-content in H-MOR

| Sample | Rate [mol((g-atom Al)h)$^{-1}$] | Space time yield [g-MeOAc(g-zeolite)h)$^{-1}$] |
|---|---|---|
| H-MOR (Zeolyst, SAR = 19.6) | 0.9 | 102.7 |
| H-MOR (Tosoh, SAR = 17.8) | 0.74 | 92.1 |
| H-MOR (Zeolyst, SAR = 19) | 0.94 | 110.4 |
| H-MOR (Sud-Chemie, SAR = 20.2) | 0.5 | 55.5 |
| H-MOR (Zeolyst, SAR = 13) | 0.99 | 162.8 |
| H-MOR (Zeolyst, SAR = 89) | 0.08 | 2.1 |

Conditions: 930 kPa CO, 20 kPa DME, 50 kPa Ar; 438 K; 3.33 cm$^3$g$^{-1}$s$^{-1}$.

General Procedures B

1) Catalyst Preparation B

A catalyst sample in the ammonium or acid form was compacted at 12 tonnes in a 33 mm die set using a Specac Press, then crushed and sieved to a particle size fraction of 212 to 335 microns. The catalyst (typically 1 g) was then calcined to convert the NH$_4^+$ form to H$^+$ form in a muffle oven (oven-volume=30 L) under a static atmosphere of air. The temperature was increased from room temperature to 450° C. at a ramp rate of 5° C./min and then held at this temperature for 12 hours.

| Zeolite precursor | Silica/Alumina Molar Ratio | Channel Structure |
|---|---|---|
| H-Mordenite-20 (Tricat) | 20 | 8 (3.4 × 4.8 Å) 8 (2.6 × 5.7 Å) 12 (6.5 × 7.0 Å) |
| NH4-Mordenite-10 (Zeolyst International) | 10 | 8 (3.4 × 4.8 Å) 8 (2.6 × 5.7 Å) 12 (6.5 × 7.0 Å) |
| NH4-Mordenite-20 (Zeolyst International) | 20 | 8 (3.4 × 4.8 Å) 8 (2.6 × 5.7 Å) 12 (6.5 × 7.0 Å) |
| NH4-Offretite-10 | 10 | 8 (3.6 × 4.9 Å) 12 (6.7 × 6.8 Å) |
| NH4-Chabazite | 7.3 | 8 (3.8 × 3.8 Å) |
| NH4-ZSM-23 | 85 | 10 (4.5 × 5.2 Å) |
| NH4-ECR-18 | 7.8 | 8 (3.6 × 3.6 Å) 8 (3.6 × 3.6 Å) |
| NH4-Theta-1 | 70 | 10 (4.6 × 5.7 Å) |
| ITQ-6 | 36.5 | 10 (4.2 × 5.4 Å) 8 (3.5 × 4.8 Å) |
| NH4- Zeolite A (Grace Davison) | 1.2 | 8 (4.1 × 4.1 Å) |
| NH4-Zeolite L | 14 | 12 (7.1 × 7.1 Å) |
| H-Mazzite | 7.7 | 8 (3.1 × 3.1 Å) 12 (7.4 × 7.4 Å) |
| NH4-BETA-18 (Zeolyst International) | 18 | 12 (6.6 × 6.7 Å) 12 (5.6 × 5.6 Å) |

The sodium form of zeolite A was converted to the NH$_4^+$ form by stirring 1 gram of material in a 10 ml solution of 1 molar ammonium nitrate for three hours and then filtering off the solution. This was repeated three times and the solid dried at 100° C. in air before pressing and sieving. The NH$_4^+$ exchanged NaA was not calcined prior to use.

Dimethyl Ether Carbonylation Reaction B

Dimethyl ether carbonylation reactions were carried out in a pressure flow reactor unit consisting of 60 identical parallel isothermal co-current tubular reactors. Into each tube 50 micro liters of catalyst was loaded onto a metal sinter having a pore size of 20 micrometers. All catalyst samples were heated at a ramp rate of 5° C./min. to 100° C. under N$_2$ at atmospheric pressure at a flow rate of 3.33 mL/ hour, and held at this temperature for 1 hour. The reactor was then pressurised to 70 barg with N2 and the system held at this condition for 1 hour. The nitrogen gas feed was then changed to a mixture comprising 64 mole % carbon monoxide, 16 mole % hydrogen and 20 mole % nitrogen at a gas flow rate of 3.33 ml/hour, and the system were heated at a ramp rate 3° C./min. to a temperature of 300° C. The system was then held at this condition for 3 hours. After this the temperature was reduced to 180° C. and allowed to stabilise for 10 minutes. At this point catalyst activation is considered complete and the gas feed was changed to a mixture comprising 64 mole % carbon monoxide, 16 mole % hydrogen, 15 mole % nitrogen and 5 mole % dimethyl ether at a gas flow rate of 3.33 ml/hour. The reaction was allowed to continue for 27.8 hours after which the temperature was increased to 250° C. The exit stream from the reactor was passed to a Varian 4900 micro gas chromatograph with three columns (Molecular Sieve 5A, Porapak® Q and CP-Wax-52) each column being equipped with a thermal conductivity detector; and an Interscience Trace gas chromatograph having two columns (CP-Sil 5 and CP-Wax 52) each equipped with a flame ionization detector. The results of the carbonylation reactions are given in Table 4.

TABLE 4

| Example | Catalyst | Reaction temperature/ °C. | Time on Stream/hrs | STY$_{MeOAc}$ g l$^{-1}$h$^{-1}$ |
|---|---|---|---|---|
| 1. | H-Mordenite-20 | 180 | 16.8 | 18 |
| 2. | | 250 | 51.6 | 16 |
| 3. | NH4-Mordenite-10 | 180 | 17.5 | 32 |
| 4. | | 250 | 52.3 | 12 |
| 5. | NH4-Mordenite-20 | 180 | 17.9 | 52 |
| 6. | | 250 | 52.7 | 99 |
| 7. | NH4-Offretite-10 | 180 | 19.6 | 55 |
| 8. | | 250 | 48.8 | 21 |
| 9. | NH4-Chabazite | 180 | 19.7 | 13 |
| 10. | | 250 | 49.0 | 0 |
| 11. | NH4-ZSM-23 | 180 | 21.2 | 1 |
| 12. | | 250 | 50.4 | 4 |
| 13. | NH4-ECR-18 | 180 | 16.0 | 25 |
| 14. | | 250 | 50.8 | 1 |
| 15. | NH4-Theta-1 | 180 | 17.3 | 0 |
| 16. | | 250 | 52.1 | 1 |
| 17. | ITQ-6 | 180 | 17.7 | 1 |
| 18. | | 250 | 52.5 | 6 |
| 19. | Na-Zeolite A | 180 | 21.4 | 0 |
| 20. | | 250 | 50.6 | 0 |
| 21. | NH4-Zeolite L | 180 | 20.3 | 0 |
| 22. | | 250 | 49.5 | 0 |
| 23. | H-Mazzite | 180 | 20.7 | 1 |
| 24. | | 250 | 49.9 | 6 |
| 25. | NH4-BETA-18 | 180 | 16.2 | 1 |
| 26. | | 250 | 51.0 | 2 |

In the above experiments, the mordenite, offretite, chabazite, ECR-18 and ITQ-6 zeolites have a silica:alumina molar ratio of at least 5, an 8-member ring channel of window size of at least 2.5 Angstroms×at least 3.6 Angstroms and at least one Bronsted acid site, and the 8-member ring channel is interconnected with a channel defined by a ring with greater than or equal to 8 members. These experiments demonstrate that significant carbonylation activity may be achieved by these zeolites. However, in the carbonylation reactions employing the zeolites, ZSM-23, Theta-1, Zeolite-A, Zeolite-L, Mazzite and Beta-18, little, if any carbonylation activity was found to occur. ZSM-23, and Theta-1 possess 10-member ring channels only and do not have 8-member ring channels; Beta-18 and Zeolite-L have 12-member ring channels only and does not have 8-member ring channels; the Zeolite-A has 8-member ring channels but its silica/alumina ratio is below 5; Mazzite has both 8- and 12-member ring channels but the 8-member ring channels do not intersect with either 8-member ring channels or 12-member ring channels.

Studies with varying concentration of Brønsted Acid Sites
H-Mordenite Catalyst Preparation NH$_4$-MOR (SiO$_2$:Al$_2$O$_3$ molar ratio ~10, Zeolyst International) samples were treated in flowing dry air (zero grade, Praxair) for 3 h at 773 K (0.0167 K s$^{-1}$) to remove residual organics and to convert NH$_4^+$ cations to H$^+$.

Na-Exchanged H-Mordenite Catalyst Preparation

NH$_4$-MOR (SiO$_2$:Al$_2$O$_3$ molar ratio ~10, Zeolyst International, approx. 14 g) was exchanged with Na using 0.5 L aqueous NaNO$_3$ (99%, EMD Chemicals, 0.014-2.44 M) at 353 K for 12 h and then washed in 2 L deionized water and isolated by filtration. The resulting solid was treated at 393 K overnight in ambient air and then in flowing dry air (zero grade, Praxair) for 3 h at 773 K (0.0167 K s$^{-1}$). The NH$_4$-MOR was exchanged with Na to prepare H$_{83}$Na$_{17}$MOR, H$_{73}$Na$_{27}$MOR, H$_{59}$Na$_{41}$MOR and H$_{45}$Na$_{55}$MOR where subscripts represent the fraction of cation-exchange sites in the parent NH$_4$-MOR sample that exist as H$^+$ or Na$^+$.

Co-Exchanged H-Mordenite Catalyst Preparation

NH$_4$-MOR (SiO$_2$:Al$_2$O$_3$ molar ratio ~20, Zeolyst International, approx.2.5 g) was exchanged with Co using 0.1 L aqueous Co(NO$_3$)$_2$.6H$_2$O(98%, Sigma-Aldrich,) at 353 K for 24 h and then washed in 0.5 L deionized water and isolated by filtration. The resulting solid was treated at ambient temperature overnight in air and then in flowing dry air (zero grade, Praxair) for 3 h at 773 K (0.0167 K s$^{-1}$). The NH$_4$-MOR was exchanged with Co to prepare H$_{29}$CO$_{32}$MOR.

H-BEA Catalyst Preparation

NH$_4$-BEA (SiO$_2$:Al$_2$O$_3$ molar ratio 12.5, Zeolyst International) was treated in flowing dry air (zero grade, Praxair) for 3 h at 773 K (0.0167 K s$^{-1}$) to remove residual organics and to convert NH$_4^+$ cations to H$^+$.

Figure 7:
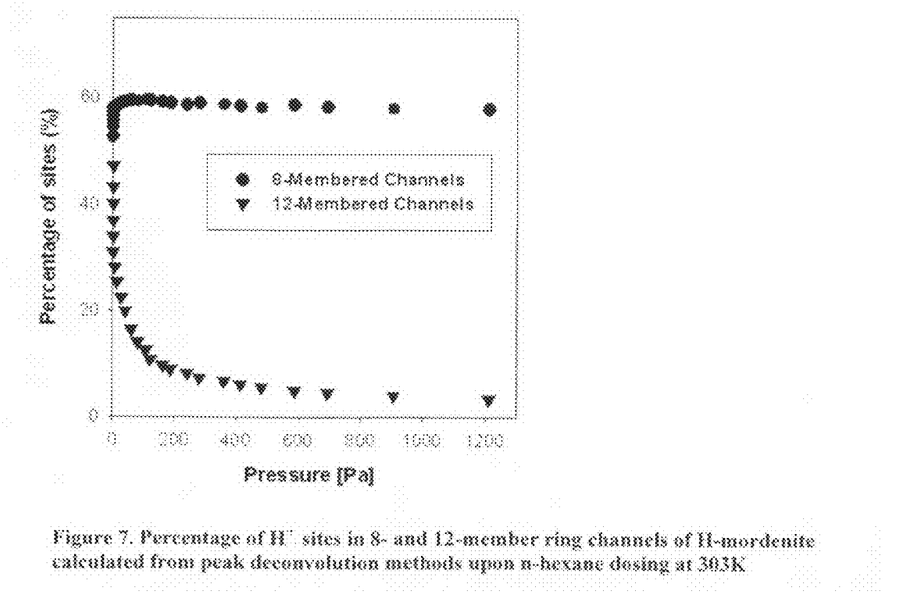
FIG. 7 depicts the percentage of $H^+$ sites in the 8- and 12-member ring channels of H-mordenite upon hexane dosing at 303 K.

Infra-red Determination of Distribution of H+ Sites in Mordenite n-Hexane was dosed at 303 K onto the H-mordenite sample, prepared as described above, to determine the concentration of H+ sites in the 8-member ring and 12-member ring channels. n-Hexane was purified by multiple freeze-thaw cycles prior to dosing. Prior to the recording of infra-red spectra, the dosed catalyst sample was treated in flowing dry air (1.67 cm$^3$s$^{-1}$, zero grade, Praxair) at 723 K for 2 hours, evacuated at 723 K for 2 hours using a diffusion pump (<0.01 Pa dynamic vacuum; Edwards E02) and cooled to ambient temperature (303 K) in vacuum. Infra-red spectra were measured on self-supporting wafers (20-40 mg) held within a quartz vacuum cell with NaCl windows using a Nicolet NEXUS 670 infra-red spectrometer equipped with a Hg—Cd—Te (MCT) detector in the 4000-400 cm$^{-1}$ frequency region. Infra-red spectra were collected at 2 cm$^{-1}$ resolution for 180 s after each dose without intervening evacuation.

n-Hexane adsorption on H-mordenite resulted in an asymmetric band in the hydroxyl region with maxima at 3610 and 3590 cm$^{-1}$. Pertubation in the 3610 cm$^{-1}$ band indicated that n-hexane accessed the H$^+$ sites in the 12-member ring channels but not in the 8-member ring channels of mordenite. As illustrated in FIG. 7 band deconvolution analysis of the obtained infrared spectra shows that 55-60% of the H$^+$ sites are located in the 8-member ring channels and 40-45% of the H$^+$ sites are located in the 12-member ring channels.

Dimethyl Ether Carbonylation using H-MOR, H-FER and Metal exchanged H-MOR Catalysts 0.5 g of each of the H-Mordenite and the Co and Na-exchanged H-mordenite catalysts, H$_{29}$CO$_{32}$MOR, H$_{83}$Na$_{17}$MOR, H$_{73}$Na$_{27}$MOR, H$_{59}$Na$_{41}$MOR and H$_{45}$Na$_{55}$MOR as prepared above, and 0.5 g of H-ferrierite (H-FER) (silica:alumina molar ratio of 68; Zeolyst International) were used to carbonylate dimethyl ether in accordance with the procedure described in Dimethyl Ether Carbonylation Reaction A above. The carbonylation rates were measured at total pressures of 1.0 MPa and 438 K (3.34 cm$^3$s$^{-1}$ g$^{-1}$). It was assumed that the total H$^+$ concentration in H-mordenite is 100H$^+$. Thus, as can be seen from FIG. 8, the carbonylation rate increases with increasing H$^+$ concentration in the 8-member rings. However, no such correlation between rate and H$^+$ concentration is observed for the 12-member rings.

Dimethyl Ether Carbonylation using H-BEA, H-MFI and H-FAU Catalysts 0.5 g of each of the zeolites H-ZSM5 (silica:alumina ratio of 25; Al—Si Penta Zeolithe GmbH) (MFI framework code), H-BEA prepared as described above and H-Y(FAU framework code) (silica:alumina ratio of 6; Engelhard Corporation)

were used to carbonylate dimethyl ether in accordance with the procedure described in Dimethyl Ether Carbonylation Reaction A above. The carbonylation rates were measured at total pressures of 1.0 MPa and 438 K (3.34 cm$^3$s$^{-1}$g$^{-1}$). The zeolite structures H-BEA and H-FAU comprise only 12-member ring channels and the zeolite structure H-MFI contains only 10-member ring channels. As can be seen from FIG. 8 the carbonylation rates for H-BEA, H-MFI and H-FAU are non-detectable.

Figure 8:
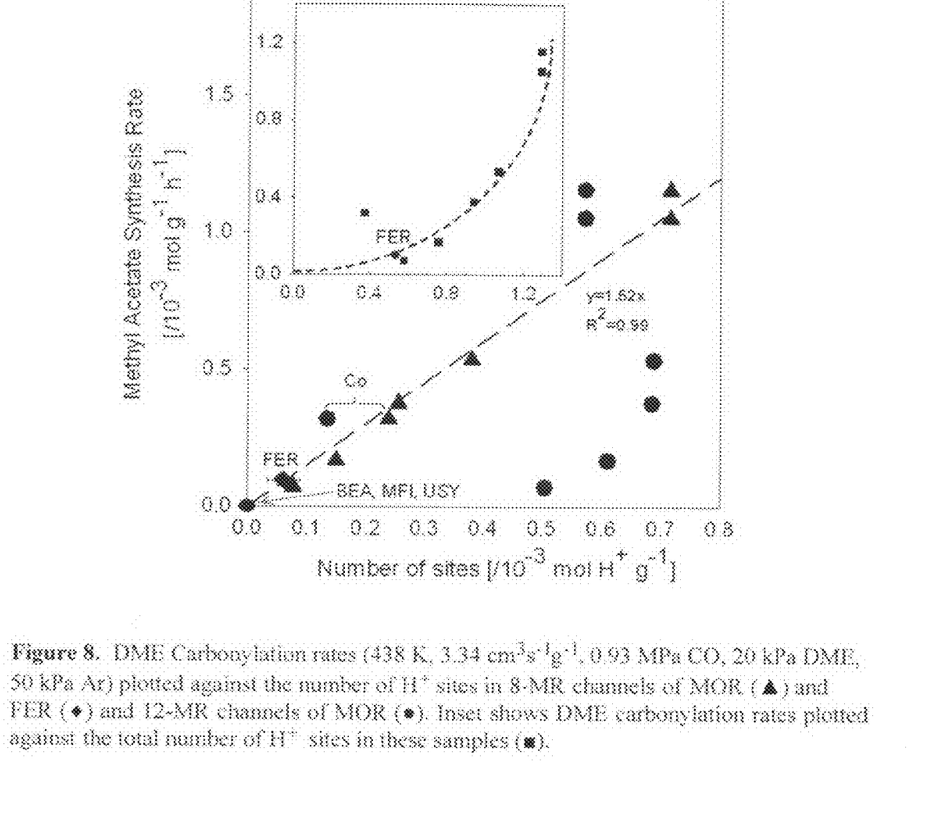
FIG. 8 depicts DME carbonylation rates normalized per proton in 8- and 12-member ring channels using H-mordenite and Na exchanged mordenite catalysts for the process of this invention.

The results shown in FIG. 8 demonstrate that the presence of H$^+$ in 8-member ring channels is consistent with the high dimethyl ether carbonylation rates observed for H-MOR and H-FER which contain 8-member ring channels and the non-detectable reactivity of H-BEA, H-MFI and H-FAU which do not contain 8-member ring channels.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process for producing a product comprising a lower alkyl ester of a lower aliphatic carboxylic acid having the formula

R$_1$—COO—R$_2$ comprising reacting a lower alkyl ether having the formula

R$_1$—O—R$_2$ in which R$_1$ and R$_2$ are independently C$_1$-C$_6$ alkyl groups, provided that the total number of carbon atoms in groups R$_1$ and R$_2$ is from 2 to 12, with a carbon monoxide-containing feed under substantially anhydrous conditions in the presence of a catalyst comprising a zeolite having at least one 8-member ring channel, said 8-member ring channel being interconnected with a channel defined by a ring with greater than or equal to 8 members, said 8-member ring having a window size of at least 2.5 Angstroms×at least 3.6 Angstroms and at least one Brønsted acid site and which zeolite has a silica:X2O3 molar ratio of at least 5, wherein X is selected from aluminium, boron, iron, gallium and mixtures thereof.

2. A process according to claim 1 in which the ester is methyl acetate and the ether is dimethyl ether.

3. A process according to claim 1 in which the zeolite catalyst is selected from the group consisting of a zeolite of framework type MOR, FER, OFF, CHA, ITE, GME, ETR, EON, and MFS.

4. A process according to claim 1 in which the temperature is from about 100° C. to about 250° C.

5. A process according to claim 1 in which the temperature is from about 150° C. to about 180° C.

6. A process according to claim 1 in which the catalyst comprises a fixed bed of catalyst.

7. A process according to claim 1 in which the catalyst comprises a fluidized bed of catalyst.

8. A continuous process according to claim 1.

9. A batch process according to claim 1.

10. A process according to claim 1 in which the carbon monoxide-containing feed further comprises hydrogen.

11. A process according to claim 10 in which the carbon monoxide-containing feed comprises a synthesis gas.

12. A process according to claim 1 further comprising hydrolyzing the ester to produce the corresponding carboxylic acid.

13. A process according to claim 2 comprising further hydrolyzing the methyl acetate to produce acetic acid.

14. A process according to claim 12 in which the hydrolysis is conducted in a separate reactor from the ester-producing reaction.

15. A process according to claim 12 in which the hydrolysis is conducted in the same reactor as the ester-producing reaction.

16. A process according to claim 1 in which R$_1$ and R$_2$ are straight chain C$_1$-C$_6$ alkyl groups.

17. A process according to claim 1 in which R$_1$ and R$_2$ are straight chain alkyl groups having from 1 to 3 carbons each.

18. A process according to claim 1 in which the alkyl groups contain a total of from 2 to 8 carbon atoms.

19. A process according to claim 18 in which the alkyl groups are straight-chain alkyl groups.

20. A process according to claim 1 in which the alkyl groups contain a total of from 2 to 6 carbon atoms.

21. A process according to claim 1 in which X is aluminium and the catalyst contains one or more additional framework metals.

22. A process according to claim 21 in which the framework metals are selected from the group consisting of gallium, boron and iron.

23. A process according to claim 21 in which the framework metal is gallium.

24. A process according to claim 21 in which the catalyst comprises mordenite and the framework metal is selected from the group consisting of gallium and boron.

25. A process according to claim 21 in which the catalyst comprises ferrierite and the framework metal is selected from the group consisting of gallium, boron and iron.

26. A process according to claim 1 wherein the catalyst is mordenite and/or ferrierite.

27. A process according to claim 26 wherein the catalyst is H-mordenite.

28. A process according to claim 3 wherein the catalyst is selected from the group consisting of offretite, gmelinite, ZSM-57 and ECR-18.

29. A process according to claim 28 wherein the zeolite is offretite.

30. A process according to claim 1 wherein the catalyst consists of channels defined solely by 8-member rings.

31. A process according to claim 1 wherein the channel defined by the 8-member ring interconnects with at least one channel defined by a ring with greater than 8 members.

32. A process according to claim 31 wherein the at least one channel defined by a ring with greater than 8 members is defined by a ring having 10 or 12 members.

33. A process according to claim 32 wherein the at least one channel defined by a ring with greater than 8 members is defined by a ring having 12 members.

34. A process according to claim 1 wherein the silica:X$_2$O$_3$ ratio is less than or equal to 100.

35. A process according to claim 1 wherein the silica:X$_2$O$_3$ ratio is in the range 7 to 40.

36. A process according to claim 1 wherein the silica:X$_2$O$_3$ ratio is in the range 10 to 30.

37. A process according to claim 1 wherein X is selected from the group consisting of aluminium, gallium and mixtures thereof.

38. A process according to claim 1 wherein X is aluminium.

39. A process according to claim 1 wherein X is aluminium and the silica:$Al_2O_3$ ratio is less than or equal to 100.

40. A process according to claim 39 wherein the silica:$Al_2O_3$ ratio is in the range 7 to 40.

41. A process according to claim 39 wherein the silica:$Al_2O_3$ ratio is in the range 10 to 30.

* * * * *